United States Patent [19]

Rao

[11] Patent Number: 4,594,241

[45] Date of Patent: Jun. 10, 1986

[54] ANTI-LEISHMANIAL PHARMACEUTICAL FORMULATIONS

[75] Inventor: Leburu S. Rao, Swanley, England

[73] Assignee: Burroughs Wellcome Co., Research Triangle Park, N.C.

[21] Appl. No.: 669,035

[22] Filed: Nov. 5, 1984

Related U.S. Application Data

[63] Continuation of Ser. No. 405,875, Aug. 6, 1982, abandoned.

[30] Foreign Application Priority Data

Aug. 10, 1982 [GB] United Kingdom ............... 8124347

[51] Int. Cl.$^4$ ..................... A61K 9/52; A61K 9/66
[52] U.S. Cl. ........................ 424/38; 424/19; 424/131; 514/943; 514/937
[58] Field of Search ..................... 424/38, 19

[56] References Cited

U.S. PATENT DOCUMENTS

| | | | |
|---|---|---|---|
| 3,960,757 | 6/1979 | Morishita et al. | 424/38 |
| 4,186,183 | 1/1980 | Steck et al. | 424/49 |
| 4,235,871 | 11/1980 | Papahadjopoulos | 424/19 |

FOREIGN PATENT DOCUMENTS

| | | |
|---|---|---|
| 53107 | 9/1974 | Australia . |
| 2015464 | 9/1979 | United Kingdom . |
| 1591306 | 6/1981 | United Kingdom . |

*Primary Examiner*—Donald B. Moyer
*Assistant Examiner*—C. Joseph Faraci
*Attorney, Agent, or Firm*—Donald Brown

[57] ABSTRACT

Antimony-containing anti-leishmaniasis drugs are encapsulated in a lipid based liposomal formulation having a weight ratio of lipid to encapsulated antimony-containing drug of 1:1.6 to 1:0.25 and a salt concentration in the continuous aqueous phase which is at least isotonic with human blood. Such formulations are found to have a leakage rate of initially encapsulated antimony-containing drug of less than 50% by weight after storage at 25° C. for 6 weeks from encapsulation and hence provide storage stable formulations which can be used effectively after prolonged storage without refrigeration in tropical climates. The anti-parasital activity of the liposomal formulations has been found greater than that of corresponding aqueous formulations. The liposomal formulations are preferably prepared by a reverse phase evaporation method involving first emulsifying an aqueous solution of the drug with an organic solvent solution of the lipid and then removing the organic solvent at reduced pressure at a temperature below the normal boiling point of the solvent but above the phase transition temperature of the lipid.

4 Claims, No Drawings

ANTI-LEISHMANIAL PHARMACEUTICAL FORMULATIONS

DESCRIPTION

This application is a continuation of application Ser. No. 405,875, filed Aug. 6, 1982, now abandoned.

This invention relates to an improved pharmaceutical formulation and is particularly concerned with new liposomal formulations of antimony-containing anti-leishmanial drugs and a process for their preparation.

Leishmaniasis is a predominantly tropical disease, the causative organism of which are species of *leishmania* which are protozoan intracellular parasites. Various antimony-containing drugs are available to combat leishmaniasis but large daily dosage levels of the antimonial drugs are necessary to combat the disease and the administration of these large amounts of these antimonial compounds may produce undesirable side effects. Some proposals have already been made for the formulation of the antimonial drugs into liposomes. Such liposomal formulations are of interest because, in principle, they are capable of targeting the drug to the cells of the reticuloendothelial system in liver, spleen and bone marrow, the major sites of the parasite infection and of providing a sustained release of the antimonial drug which normally has to be administered parenterally. This means that there can be opportunities, with liposomal formulation, for more effective use of the antimonial compound and so reduce the overall dosage level that needs to be administered and/or the number of occasions that the drug needs to be injected. However, the liposomal formulations that have been proposed so far suffer from the disadvantage of relatively low levels of incorporation of the antimonial drug in the liposome and/or relatively high leakage rates of the antimonial drug from the encapsulated aqueous phase into the continuous aqueous phase on storage. This means that the existing liposome formulations need to be prepared just before use.

We have now found that by careful control of the ratio of the antimonial drug to the lipid forming the liposomal walls, and the composition of the external continuous aqueous phase, it is possible to produce liposomal formulations of antimonial drugs which contain large amounts of encapsulated drug and which are storage stable so that effective therapy can be achieved by the injection of smaller dosage volumes of the liposomal formulation from "off the shelf" stock.

Accordingly, the present invention provides a lipid based liposomal formulation of an antimony-containing anti-leishmaniasis drug having a leakage rate of initially encapsulated antimony-containing drug of less than 50% by weight after storage at 25° C. for 6 weeks from encapsulation and in which the weight ratio of the lipid to the encapsulated antimony-containing drug is from 1:1.6 to 1:0.25 and wherein the continuous aqueous phase contains a pharmaceutically acceptable salt present in a concentration at least isotonic with human blood.

The antimony-containing drugs which can be formulated in accordance with the present invention are any of the antimony-containing drugs conventionally used to combat leishmaniasis. The drug most commonly used for this purpose is sodium stibogluconate (SSG) which is sold under the name Pentostam. Other antimony-containing drugs which are used to combat leishmanaisis and which can be formulated in accordance with the present invention are meglumine antimoniate (known as Glucantime), potassium antimony tartrate or urea stibamine.

The lipid materials used in the formulation of the present invention may be any of those conventionally used in liposomal formulations. In order to form a stable liposome, we find it convenient to use at least one phospholipid and this may be phosphatidyl choline or, preferably, dipalmitoylphosphatidyl choline. Other lipid materials that may be used in the formulation of the liposomes include cholesterol, dicetyl phosphate, phosphatidic acid, lysophosphatidylcholine, phosphatidylserine, phosphatidylethanolamine, phosphatidylglycerol, sphingolipids, glycolipids etc. or a combination of two or more such lipid materials.

We have found that a particularly useful combination of lipids that can be used in our formulations is a mixture of dipalmitoylphosphatidylcholine, cholesterol and dicetylphosphate in a 4.5:4.5:1 molar ratio. Other specific lipid mixtures which can be used are the same three lipids mentioned above but in a molar ratio of 2:1.5:0.22 and other ternary mixture comprising phosphatidylcholine:cholesterol:diacetylphosphate in a molar ratio of 7:2:1.

Conventional methods for the encapsulation of antimony-containing drugs in liposomal formulations have resulted in the encapsulation of somewhere in the region of 2 to 10% of the drug contained in the initial aqueous phase. Since there is inevitably some leakage of the encapsulated drug during storage and, in previous liposomal formulations of antimonial drugs, this leakage rate during storage has been excessively high, this has meant that extremely large dosage volumes of the liposomal formulation have had to be injected in order to introduce a sufficient quantity of antimonial drug. We have now found that by a variation of the reverse phase evaporation method, we can secure levels of encapsulation of the antimonial drug in excess of 50% of the drug contained in the initial aqueous phase and this, coupled with the significantly reduced leakage of encapsulated material from the liposomes during storage means that therapeutically effective dosages of the antimony compound can be injected using "off-the-shelf" formulations in substantially reduced dosage volumes. The modified reverse phase evaporation method that we have used involves dissolving the lipid component or components in an organic solvent, e.g. chloroform and emulsifying this organic phase with an aqueous solution containing the antimony drug. This emulsification can be achieved simply by stirring the organic phase and aqueous phase together with one another at an elevated temperature above the phase transition temperature of the lipid but below the boiling point of the organic solvent used to introduce the lipid component. A metastable emulsion can be formed in this way and the organic solvent is then moved from the metastable emulsion by evaporation, under reduced pressure if necessary so that all of the organic solvent can be removed at a temperature which is below boiling point of the solvent but above the phase transition temperature of the lipid. We have found that by operating in this way, the emulsion initially takes on a gel-like appearance but that, when all of the organic solvent has been removed, a normal milky liposomal dispersion exists in which subsequent tests show that about 40% to 60% of the antimony compound initially present in the aqueous phase is encapsulated inside the liposomal formulations.

In accordance with the present invention, the weight ratio of the lipid to the encapsulated antimony compound is 1:1.6 to 1:0.25. The liposomal formulations of the invention contain significantly more encapsulated drug than do the conventional liposomal formulations and consequently, the weight ratio of the drug to the lipid material is much higher in the formulations of the invention than in the conventional liposomal formulations. Our initial experiments indicated that satisfactory results could be obtained with a lipid:drug weight ratio of 1:0.5 but since it is clearly desirable to have the drug:-lipid ratio as high as possible in order to reduce the eventual dosage volume that needs to be injected, we conducted further experiments in which we increased the concentration of the drug in the original aqueous phase and found that we could still achieve stable formulations in which the lipid:drug weight ratio had increased to 1:1 or even to 1:1.5.

The liposomes of the invention, obtained by the modified reverse phase evaporation method described above, will normally comprise predominantly a mixture of oligolamellar and multilamellar vesicles. The average diameter of the liposomes will normally be about 0.9–2.3 μm, preferably about 1.3–1.8 μm. Liposomal diameter has not been found to alter significantly during storage.

Regardless of the method used for formation of the liposomes, there will inevitably be significant amounts of drug which are not encapsulated into the liposomes but remain in the continuous aqueous phase. For various reasons, it is often desirable to remove the drug from the continuous aqueous phase and this is conveniently done either by dialysing the liposomal formulation against a drug-free aqueous phase across a dialysis membrane or by centrifugation. We have found that unencapsulated drug can be easily removed from the continuous aqueous phase by dialysis against 5 to 15 times, conveniently 10 times the volume of drug-free aqueous phase over a 24 hour period with two or three changes of the drug-free aqueous phase during this period to ensure that substantially all the unencapsulated drug is removed from the liposomal formulation. Centrifugation is preferably carried out at up to 5,000 rpm for up to 30 minutes. Most of the supernatant containing unencapsulated drug is then separated from the liposomal pellet with minimum disturbance of the pellet. The pellet can be redispersed in fresh drug-free aqueous salt solution and the centrifugation, separation of the supernatant and redispersal of the pellet in fresh drug-free aqueous salt solution repeated until the supernatant is substantially drug-free. Unencapsulated drug can also be removed from the continuous aqueous phase by column chromatography.

For experimental purposes, once substantially all the unencapsulated drug has been removed from the continuous aqueous phase, it is possible to determine the leakage rate of the encapsulated drug into the continuous aqueous phase. It is important in the formulations of the invention that the continuous aqueous phase contains a salt solution in a concentration which is at least isotonic to human blood and is preferably at least double the isotonic concentration. We have found that the leakage rate of the encapsulated drug into the continuous phase is influenced by the presence of this salt in the continuous aqueous phase and we have found that alkali metal salts, particularly sodium chloride is the most satisfactory material to use for this purpose although alkaline earth metal salts, particularly calcium chloride can also be used. Since the formulation will normally be injected into patients, it is important that the concentration of the salt be at least isotonic with human blood and our experiments have indicated the desirability of using 0.9% w/v sodium chloride in the continuous aqueous phase. The use of salt concentrations in excess of the isotonic concentration is often necessary, particularly when the drug:lipid ratio is towards the higher end of the range 0.25:1 to 1.6:1, in order to control the leakage rate of the drug so that not more than 50% of the originally encapsulated drug leaks out after storage at 25° C. for 6 weeks but the benefits of reduced leakage have to be counterbalanced against the disadvantage of injecting too high a concentration of sodium chloride into a patient's bloodstream.

As an alternative to the use of inorganic salts such as sodium chloride or calcium chloride in the continuous aqueous phase, it is also possible to use organic salts such as sodium citrate, again at concentrations at least isotonic with human blood.

We have found that the pH of the continuous aqueous phase is a factor of importance in relation to the lipid stability of the liposomal formulation and that, for prolonged storage stability with minimum leakage of encapsulated drug, the pH should be at least about 4 but not more than about 8 and preferably in the range of about 5.5 to 7, e.g. 6.5.

When sodium citrate is used as the salt in the continuous aqueous phase, the pH of this continuous aqueous phase is found to be about 6.1 to 6.2 so that the addition of a pH adjusting agent to the continuous aqueous phase is not really necessary. On the other hand, the use of sodium chloride as the salt in the continuous aqueous phase gives rise to a pH of about 4 to 5 in the continuous aqueous phase and in such cases, improved lipid stability with reduced leakage of encapsulated drug can be secured by the addition of a basic compound in sufficient quantities to increase the pH of the continuous aqueous phase to 5.5 to 7. Typically, the basic compound will be an alkali metal hydroxide such as sodium hydroxide but the function of the basic compound is merely to raise the pH of the continuous aqueous phase to the desired level and any physiologically acceptable organic or inorganic base of pH more than 7 can, in principle, be used.

The leakage of the encapsulated drug from the liposome into the continuous aqueous phase is a complicated phenomenon influenced not only by the nature and concentration of the salt present in the continuous aqueous phase but also by the amount of encapsulated drug and the nature and proportions of the lipids used for the production of the liposomes. Some leakage of encapsulated drug after liposome formation is inevitable but we have found that provided that the lipid to encapsulated drug ratio is within the limits indicated above and there is an appropriate salt concentration in the continuous aqueous phase that the leakage of encapsulated drug that does occur occurs only within the first few days of storage and that after a few days, the liposomal formulation equilibrates and there is no further leakage of encapsulated drug into the continuous aqueous phase. This means that, provided the formulations are stored at temperatures not exceeding about 40° C., the formulations can be stored for 3 to 6 months with leakage rates well below 50%. This is of great practical importance since it means that the formulations can be stored without refrigeration in tropical climates and can be injected in acceptable dosage volumes to introduce liposomal formulations having a known concentration of encapsulated drug which differs very little from the concentration present in the formulation after the main drug leakage during the first few days storage had occurred.

The synthetic methods used for the preparation of the liposomes described above give rise to so-called negatively charged liposomes which are generally preferred over positively charged liposomes for reasons of toxicity and interactions with plasma. Negative liposomes are also found to be preferable as they appear to have a repulsive effect on the antimony-containing anion which may be hindered in its passage throug the bilayer in vivo.

The liposomal formulations of the invention may also contain anti-bacterial agents in the aqueous phase and we have found that the stability characteristics of our liposomes are unaffected by the incorporation of 0.1% v/v 38% formaldehyde solution to prevent microbial contamination. Alternatively, for clinical use, the formulations of the invention may be prepared in sterile form and packaged aseptically for storage.

The following Examples are given to illustrate the invention.

EXAMPLE 1

A solution of lipids was prepared by dissolving 0.24 g synthetic dipalmitoylphosphatidylcholine, 0.124 g cholesterol and 0.036 g dicetylphosphate in 40 ml chloroform. The molar ratio of the three lipid materials was 4.5:4.5:1. This solution was placed in a water-bath maintained at 45°–50° C. and a silverson stirrer with a tubular stirring head was used to provide agitation. 12 ml of deionised water containing 0.4 g sodium stibogluconate (SSG) was added to the lipid solution gradually over 10 minutes. Stirring was maintained and continued during the addition and continued for 5 minutes after the addition was completed. The resulting metastable emulsion was transferred to a rotary evaporator and the chloroform removed under reduced pressure at 45°–50° C. When most of the solvent had been removed, the dispersion had a gel-like appearance. Continued evaporation removed all of the chloroform when a normal milky liposomal dispersion remained. This dispersion was transferred to a 20 ml volumetric flask and sufficient concentrated saline was added to give a 0.9% w/v sodium chloride concentration in the 20 ml dispersion.

The liposomal dispersion was introduced into a dialysis bag of Visking tubing 18/32 and the bag sealed. The sealed bag was then placed in 200 ml of 0.9% w/v sodium chloride solution and agitated at 25° C. After 3 hours, the 200 ml saline was discarded and replaced with 200 ml of fresh saline and after a further 16 hours, this saline was discarded and replaced by a further 200 ml of fresh saline. The dialysis was terminated after a further 3 hours and the volume of the liposomal dispersion then measured. The degree of encapsulation of SSG was measured at this stage and was found to be 58.8% of the SSG originally introduced. As the starting SSG contained 15% moisture, the weight ratio of lipid to encapsulated SSG in this experiment was 1:0.5.

The liposomal formulation was stored at 25° C. and leakage rates of encapsulated SSG were measured weekly for 6 weeks. The leakage was determined in the following way. A 3 ml sample of the formulation was placed in a polycarbonate tube with a stopper and centrifuged at 20,000 rpm for 20 minutes. The pellet was then resuspended in 0.9% w/v saline and a total of three centrifugations carried out and the supernatants from the first centrifugation and the two washing steps combined and made up to 25 ml in deionised water. The twice-washed liposome pellet was also dispersed in deionised water and made up to 10 ml and the samples of the supernatant and the diluted liposome pellet were then assayed for antimony. This assay was done on a Perkin Elmer 305 atomic absorption spectrophotometer and the following results were obtained:

TABLE

| Number of days storage | SSG content in mg. | | | Leakage, i.e. SSG in supernatant as % of total |
|---|---|---|---|---|
| | Supernatant | Liposome Pellet | Total | |
| 14 | 4.7 | 16.7 | 21.4 | 22.0 |
| 21 | 5.1 | 17.5 | 22.6 | 22.6 |
| 28 | 5.0 | 17.5 | 22.5 | 22.2 |
| 35 | 5.0 | 17.3 | 22.3 | 22.4 |
| 42 | 5.2 | 17.0 | 22.2 | 23.4 |

These results show that although some leakage of encapsulated SSG occurs, substantially all of this leakage occurs within the first 2 weeks storage and substantially no further leakage occurs after that time.

EXAMPLE 2

The procedure described in Example 1 was repeated using the same lipid mixture but using different weights of lipid and of SSG. The ratio of the volumes of the aqueous phase and the solvent phase were kept constant by dissolving the lipid in sufficient chloroform to form a 1% w/v solution and the SSG in water to form a 10% w/v solution. In Preparations 7 to 9 where 2 g. of lipid and 3 g. of drug were used, the same 100 ml quantity was used resulting in a 2% w/v solution of the lipid. In certain experiments, as indicated below, the NaCl concentration in the continuous aqueous phase was increased to 1.8% w/v (twice isotonic) or 2.7% w/v (three times isotonic), or the NaCl was replaced by $CaCl_2.2H_2O$ used in a concentration in the continuous aqueous phase of 3.4% w/v (twice isotonic) or 5.1% w/v (three times isotonic) or by sodium citrate in a continuous aqueous phase concentration of 6.0% w/v (twice isotonic). The milky liposomal dispersion was made up to 50 ml (20 ml in Preparation No. 2) with water and salt to give the desired final salt concentration in the continuous aqueous phase. The formulations also had 0.1% v/v 38% formaldehyde solution introduced, after the dialysis step, to combat microbial contamination.

The unencapsulated SSG was removed by dialysis as described in Example 1 and the degree of encapsulation and the leakage rates during storage at 25° C. were determined as described in Example 1. The results obtained are summarised in the following Tables:

TABLE 1

| Preparation Number | Lipid Mixture g | Nominal weight of SSG. g | Weight ratio lipid:SSG | External medium composition |
|---|---|---|---|---|
| 1 | 1.0 | 3.0 | 1:1.487 | 1.76% $CaCl_2.2H_2O$ |
| 2 | 0.4 | 1.2 | 1:1.475 | 1.76% $CaCl_2.2H_2O$ |
| 3 | 1.0 | 3.0 | 1:1.063 | 1.8% NaCl |
| 4 | 1.0 | 3.0 | 1:1.341 | 3.4% $CaCl_2.2H_2O$ |
| 5 | 1.0 | 3.0 | 1:1.108 | 2.7% NaCl |
| 6 | 1.0 | 3.0 | 1:1.082 | 5.1% $CaCl_2.2H_2O$ |
| 7 | 2.0 | 3.0 | 1:0.622 | 1.8% NaCl |
| 8 | 2.0 | 3.0 | 1:0.667 | 3.4% $CaCl_2.2H_2O$ |

TABLE 1-continued

| Preparation Number | Lipid Mixture g | Nominal weight of SSG. g | Weight ratio lipid:SSG | External medium composition |
|---|---|---|---|---|
| 9 | 2.0 | 3.0 | 1:0.701 | 6.0% sodium citrate |

TABLE 2

| Preparation No. | Volume after dialysis, ml. | Encapsulated SSG. g | % Encapsulation | SSG retained in test period mg/ml | Total, g | g/g of lipid | Leaked % (mean) |
|---|---|---|---|---|---|---|---|
| 1 | 67 | 1.487 | 55.3 | 11.5 | 0.772 | 0.77 | 48.1 |
| 2 | 27 | 0.590 | 57.7 | 12.1 | 0.326 | 0.82 | 44.7 |
| 3 | 73 | 1.063 | 38.7 | 7.7 | 0.560 | 0.56 | 47.4 |
| 4 | 65 | 1.341 | 51.3 | 14.5 | 0.940 | 0.94 | 30.4 |
| 5 | 70 | 1.108 | 41.3 | 8.7 | 0.607 | 0.61 | 45.3 |
| 6 | 55 | 1.082 | 45.5 | 13.2 | 0.724 | 0.72 | 33.1 |
| 7 | 68 | 1.244 | 52.9 | 13.3 | 0.904 | 0.45 | 27.3 |
| 8 | 65 | 1.335 | 55.8 | 16.0 | 1.038 | 0.52 | 22.2 |
| 9 | 63 | 1.403 | 52.3 | 16.3 | 1.029 | 0.51 | 26.2 |

Using the various relative proportions of lipid and SSG as described in this Example, percent encapsulation was between 38 and 57%. These encapsulation degrees enabled the leakage rate of the formulations to be determined and the results given in Table 2 above show the average leakage after storage at 25° for 7 weeks.

Animal Test

Inbred male mice, strain Balb/c (Bantin & Kingman), were infected with *Leishmania donovani* by intravenous inoculation of $10^7$ amastigotes from the spleen of an infected hamster. One week after inoculation, the mice were divided into groups of 9–10 animals and dosed intravenously into the tail vein with sodium stibogluconate, either as free drug or entrapped in liposomes similar to those described in Example 1. The dose was given once daily for 5 days. Empty liposomes were inoculated into one group as controls. Seven days after the first dose of drug, the mice were killed, the livers excised and weighed, and impression smears prepared from a cut surface of the liver. The impression smears were stained with Giemsa, and number of amastigotes counted microscopically per 500 liver cell nuclei, and the total number of parasites calculated by the method of Stauber et al. J. Protozoology, 5, 269, (1958).

The doses of sodium stibogluconate were calculated in terms of mg antimony/kg for both free and entrapped drug. The liposome dilutions were freshly prepared for each day of drug treatment.

The results of treatment are expressed as the mean of the total numbers of amastigotes in the liver of each mouse. The following results were obtained:

TABLE 3

Effect of liposome entrapped sodium stibogluconate on Balb/c mice infected with *L. donovani* (expt. 44)
Treatment given daily for 5 days and by the intravenous route

| Treatment | Dose level mg Sb/kg × 5 | Mean no. of parasites/mouse liver ± SE × $10^8$ | % inhibition |
|---|---|---|---|
| Untreated | — | 5.55 ± 0.59 | — |
| Blank liposome | — | 6.73 ± 0.67 | — |
| Sodium stibogluconate | 15 | 0.38 ± 0.08 | 93 |
|  | 5 | 1.54 ± 0.21 | 72 |
| Sodium stibogluconate liposomes | 13 | 0.02 ± 0.01 | 100 |
|  | 1.3 | 0.020 ± 0.010 | 100 |
|  | 0.13 | 0.52 ± 0.05 | 92 |
|  | 0.013 | 6.07 ± 0.29 | 10 |

TABLE 4

Effect of liposome entrapped sodium stibogluconate on Balb/c mice infected with *L. donovani* (expt. 56)
Treatment given daily for 5 days and by the intravenous route.

| Treatment | Dose level mg Sb/kg × 5 | Mean no. of parasites/mouse liver ± SE × $10^8$ | % inhibition |
|---|---|---|---|
| Untreated |  | 4.91 ± 0.56 | — |
| Blank lipsomes |  | 5.28 ± 0.36 | — |
| Sodium stibogluconate | 4.0 | 0.35 ± 0.11 | 93 |
|  | 2.0 | 1.55 ± 0.36 | 69 |
|  | 1.0 | 3.65 ± 0.29 | 26 |
|  | 0.5 | 3.80 ± 0.37 | 23 |
| Sodium stibogluconate liposomes | 0.2 | 0.29 ± 0.08 | 95 |
|  | 0.1 | 0.74 ± 0.26 | 86 |
|  | 0.05 | 2.00 ± 0.17 | 62 |
|  | 0.025 | 2.88 ± 0.32 | 54 |

TABLE 5

| Treatment | $ED_{50}$ (P95 limits) mg Sb/kg × 5 | Potency relates to free drug (P95 limits) |
|---|---|---|
| Expt. 44 |  |  |
| Free sodium stibogluconate | 2.4 (3.2–1.8) | 1 |
| Liposome entrapped sodium stibogluconate | 0.079 (0.098–0.063) | 30.4 (42.6–21.3) |
| Expt. 56 |  |  |
| Free sodium stibogluconate | 1.14 (1.35–0.95) | 1 |
| Liposome entrapped sodium stibogluconate | 0.034 (0.041–0.027) | 33.6 (43.8–26.3) |

The results given in Table 4 used closer spaced doses than those of the results in Table 3. Analysis of the parasite counts (Table 5) shows that the liposome entrapment of SSG increased the activity against the liver parasites by 30 to 34 times.

EXAMPLE 3

The procedure described in Example 2 for Preparation No. 7 was repeated up to the stage of addition of the water and sodium chloride to the milky liposomal dispersion. 50 ml portions of the dispersion were then centrifuged at ambient temperature at 4,000 rpm for 15 minutes and the supernatant removed as far as possible without disturbing the pellet of liposome. Fresh drug-free 1.8% w/v sodium chloride solution was then added to the pellet to bring the volume back to 50 ml, the pellet was dispersed in the solution and the dispersion centrifuged again as described above. The supernatant was then removed as described above and the washing procedure with fresh saline bringing the volume back to 50 ml, dispersal and centrifugation procedure was repeated as described above. The liposomal pellet was then redispersed in a volume of drug-free 1.8% w/v sodium chloride solution sufficient to bring the volume of the dispersion back to 50 ml and 0.1% v/v of a 38% w/v solution of formaldehyde was added and this dispersion, designated Preparation No. 10, subjected to the same tests as described in Example 2 to determine leakage rate during storage at 25° C.

Preparation No. 10 was found to contain 1.015 g encapsulated drug which gives a degree of encapsulation of 39.5%. Over the test period of 7 weeks storage at 25° C., Preparation No. 10 showed 19.4 mg drug/ml retained. This corresponds to a total weight of SSG of 0.970 g or 0.49 g/g of lipid. The average percentage leakage over this 7 week storage period of encapsulated SSG is therefore only 4.2%.

EXAMPLE 4

Further animal tests on mice, as described in Example 2, were carried out using a liposomal formulation corresponding to that described as Preparation No. 8 in Example 2. The regime described in Example 2 was changed however in that, instead of injecting the groups of mice on 5 consecutive days, the mice were injected on one single occasion with a dose 5 times as large as the daily dose rate. Tests were carried out on groups of mice given various dosage rates as indicated in Tables 3 and 4 above so that $ED_{50}$, the dosage rate necessary to reduce the parasite count to 50% of the untreated group, could be calculated. The results of our Experiment No. 82 show that an $ED_{50}$ value for liposomal drug was 0.174 mg antimony per kilogram body weight. This is to be compared with an $ED_{50}$ value for the conventional unencapsulated drug of 61.2 mg antimony per kilogram body weight. This result shows that the liposomal entrapment of the drug increased the activity against liver parasites by some 350 times.

Toxicity Test

A liposomal formulation of the type described in Example 1 was administered to mice of the type described in Example 2 and by the intravenous route on 7 consecutive days. The amount of liposomal formulation administered corresponded to a daily dose of 13 mg antimony/kg body weight. There was no overt evidence of toxicity in the mice after the 7 daily administrations.

I claim:

1. A pharmaceutical formulation consisting essentially of an anti-leishmanial effective amount of sodium stibogluconate encapsulated in liposomes consisting of dipalmitoylphosphatidyl choline, cholesterol and dicetyl phosphate in a molar ratio of 4.5:4.5:1 respectively, the weight ratio of the lipid mixture to encapsulated said sodium stibogluconate being from 1:1.6 to 1:0.25 said liposomes being suspended in a continuous aqueous phase containing a pharmaceutically acceptable salt and having a tonicity at least twice that of human blood and having a pH of about 5.5 to 7 whereby the leakage rate of initially encapsulated sodium stibogluconate is less than 50% by weight after storage at 25° C. for 6 weeks from encapsulation.

2. A formulation according to claim 1 wherein the lipid mixture:encapsulated drug weight ratio is 1:1.5 to 1:0.5.

3. A formulation according to claim 1 wherein the diameter of the liposomes is about 0.9 to 2.3 μm.

4. A formulation according to claim 1 wherein said pharmaceutically acceptable salt is sodium chloride present in a concentration such that the tonicity of the continuous aqueous phase is at least twice that of human blood.

* * * * *